(12) United States Patent
Iddan et al.

(10) Patent No.: US 6,632,171 B2
(45) Date of Patent: Oct. 14, 2003

(54) METHOD FOR IN VIVO DELIVERY OF AUTONOMOUS CAPSULE

(75) Inventors: Gavriel J. Iddan, Haifa (IL); Gavriel Meron, Petach Tikva (IL)

(73) Assignee: Given Imaging Ltd., Yoqneam Ilite (IL)

( * ) Notice: Subject to any disclaimer, the term of this patent is extended or adjusted under 35 U.S.C. 154(b) by 0 days.

(21) Appl. No.: 10/241,773

(22) Filed: Sep. 12, 2002

(65) Prior Publication Data

US 2003/0013938 A1 Jan. 16, 2003

Related U.S. Application Data

(63) Continuation of application No. 09/582,037, filed as application No. PCT/IL98/00621 on Dec. 22, 1998, now abandoned.

(30) Foreign Application Priority Data

Dec. 22, 1997 (IL) ................................................ 122716

(51) Int. Cl.[7] ................................................ A61B 1/00
(52) U.S. Cl. ........................ 600/106; 600/104; 600/101
(58) Field of Search .................................... 600/101, 104, 600/106, 129, 127

(56) References Cited

U.S. PATENT DOCUMENTS

| 4,027,510 | A | 6/1977 | Hiltebrandt |
| 4,198,960 | A | 4/1980 | Utsugi |
| 4,278,077 | A | 7/1981 | Mizumoto |
| 5,373,840 | A | 12/1994 | Knighton |
| 5,604,531 | A | 2/1997 | Iddan et al. |
| 5,607,435 | A | 3/1997 | Sachdeva et al. |
| 5,653,677 | A | 8/1997 | Okada et al. |
| 5,674,179 | A | 10/1997 | Bonnet et al. |
| 5,681,279 | A | 10/1997 | Roper et al. |

FOREIGN PATENT DOCUMENTS

| JP | 7275197 | 10/1995 |

*Primary Examiner*—John P. Leubecker
(74) *Attorney, Agent, or Firm*—Eitan, Pearl, Latzer & Cohen Zedek, LLP

(57) ABSTRACT

A method for inserting an autonomous capsule into the G.I. tract includes use of an endoscope having a clamp and at least one retractable support for retaining the clamp. The capsule is engaged with the clamp and pushed to its desired position within the G.I. tract. The capsule is then disengaged by loosening the hold of the clamp on the capsule. The insertion of the capsule can be observed through an imaging unit placed within the endoscope.

2 Claims, 4 Drawing Sheets

METHOD FOR IN VIVO DELIVERY OF AUTONOMOUS CAPSULE

CROSS-REFERENCE TO RELATED APPLICATIONS

This application is a continuation of U.S. patent application Ser. No. 09/582,037, filed Jun. 21, 2000, now abandoned, which is hereby incorporated by reference, entitled "SYSTEM AND METHOD FOR IN VIVO DELIVERY OF AUTONOMOUS CAPSULE", which in turn claims benefit from prior International Application No. PCT/IL98/00621 entitled "SYSTEM AND METHOD FOR IN VIVO DELIVERY OF AUTONOMOUS CAPSULE", filed Dec. 22, 1998, which in turn claims benefit from prior Israeli application No. 122716 entitled "SYSTEM AND METHOD FOR IN VIVO DELIVERY OF AUTONOMOUS CAPSULE" filed Dec. 22, 1997.

FIELD OF THE INVENTION

The present invention concerns a delivery system for autonomous capsules used in internal imaging of the gastrointestinal tract.

BACKGROUND OF THE INVENTION

Endoscopic inspection is a common practice in the medical diagnosis of gastro-intestinal (G.I.) diseases. According to such a method, the video camera used for identifying observable irregularities of the internal lining of the G.I. tract is installed within an endoscope, with progressive scenes observed by pushing the endoscope inside the tract. The endoscope is a tubular device typically containing an image collecting device, a light source and optionally a remotely controlled mechanical appliance for sampling tissue and for manipulating the endoscope tip. A device such as the tissue sampler, which is a claw-like utility for picking out tissue parts for purposes such as biopsies, is generally manipulated by a cable or a rod. For that purpose, endoscopes often comprises a bore for housing such longitudinal mechanical power drivers.

Because the movement of the endoscope head along the G.I. tract is brought about by a pushing action, there are affects associated with the application of force which become especially adverse as bends in the G.I. tract impede the movement of the endoscope. The G.I. tract walls at the bends become susceptible to perforation, making the internal in vivo application of probes, notably endoscopes, limited in use to non-convoluted regions of the G.I. tract.

An in-vivo autonomous capsule, such as the one described in U.S. Pat. No. 5,604,531, moves along the G.I. tract by virtue of the natural squeezing action of the tract's walls, thus overcoming the risk associated with the pushing. Another advantage arising from the employment of such an autonomous device, is that it offers a much more convenient method of administering a sensor to the G.I. tract, overcoming the cumbersome aspects of connecting the intestines of the patient to external appliances. Thus, data signals, typically electronic, of the gastro-intestinal tract are obtained without physical connections being made to an energy source or a physical information download link. Autonomous capsules are potentially convenient and useful tools for acquiring information of the inner lining of the G.I. tract, being especially beneficial for searching the small intestines which are highly convoluted. Other autonomous capsule types are used in medicine, such as pH measuring, motility measuring, pressure measuring, and those used for internal administration of medicaments.

SUMMARY OF THE PRESENT INVENTION

It is an object of the present invention to provide a device and method for inserting an autonomous capsule in the G.I. tract, in a manner that the capsule begins its autonomous journey in the small intestines, while obviating the need to travel along the upper part of the G.I. tract.

In accordance with a preferred embodiment of the invention, a device is provided for delivering autonomous capsules into the G.I. tract. Such a device includes an endoscope having a longitudinal axis and a clamp for releasably holding the capsule whereby its longitudinal axis lies along the same axis as the longitudinal axis of the endoscope. The clamp is held in the front of the endoscope by at least one support. A forward looking imaging unit is also situated at the front end of the endoscope, In accordance with a preferred embodiment of the invention, the clamp is ring shaped such that its inner radius holds the capsule tightly.

In an alternative embodiment, the clamp is a tissue sampler.

Additionally, in accordance with a preferred embodiment of the invention, there is provided a method for inserting an autonomous capsule into the G.I. tract using an endoscope. The endoscope has a clamp and at least one retractable support for retaining the clamp. The method includes the steps of:

engaging the capsule with the clamp;

pushing the capsule to its desired position within the G.I. tract; and disengaging the capsule by loosening the hold of the clamp on the capsule.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

Figure 1:
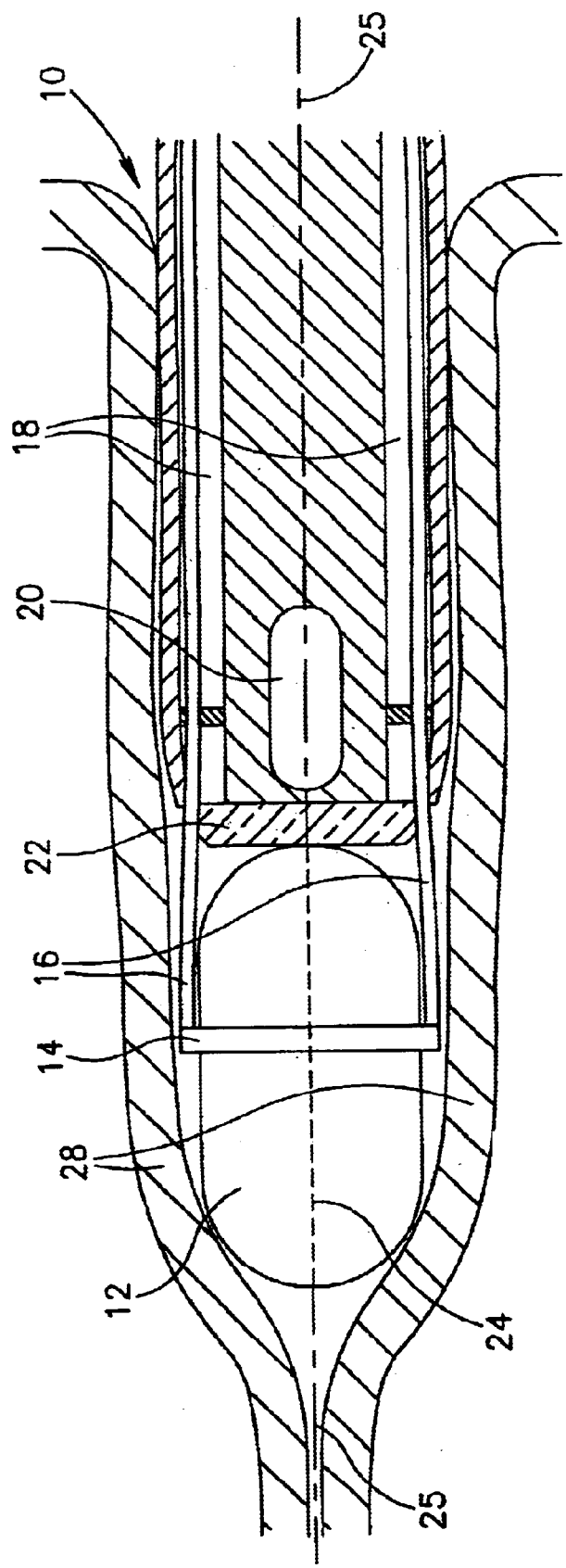
FIG. 1 is a schematic illustration of a delivery system for inserting autonomous capsules for data collecting, in the G.I. tract.

Reference is now made to FIG. 1, which schematically shows a modified endoscope 10 engaging a capsule 12, constructed and operative in accordance with a preferred embodiment of the present invention. The endoscope device 10, shown inserted tightly within the walls of a G.I. tract 28, comprises a ring clamp 14 with retractable supports 16. The endoscope 10 also comprises a camera (imager) 20, for taking images through an optical window 22.

The capsule 12 is attached to the front of the endoscope with its longitudinal axis 24 parallel (and in line with) to the longitudinal axis 25 of the endoscope. The capsule 12, which abuts window 22, is held in place by the ring clamp 14, which is itself supported by the pair of retractable supports 16. Retractable supports 16 are movable within a bore 18, along the entire length of the endoscope 10.

The modified endoscope 10 of the invention can insert an autonomous capsule 12 in a target location within the G.I. tract 28 in a manually controlled fashion, thereby achieving several goals. In particular, endoscope 10 can be used to expeditiously insert the autonomous capsule 12 in a desired location, thus reducing the time required for the autonomous capsule to reach its target. As a result, the autonomous capsule has more time in which to collect data. The modified endoscope can be used in the non-convoluted terminal of the G.I. tract.

Figure 2:
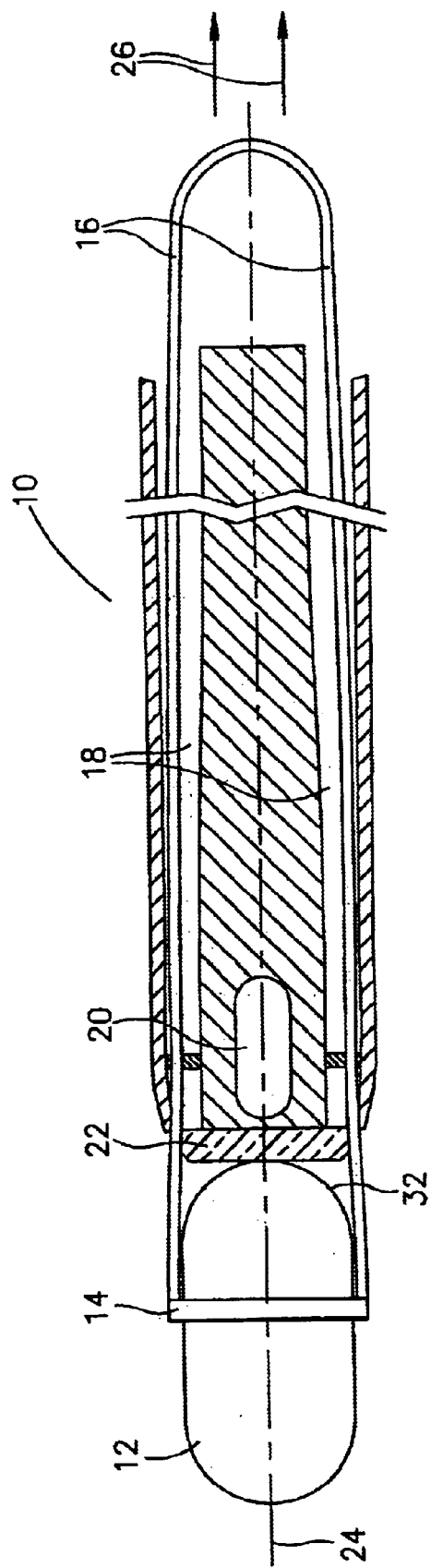
FIG. 2 is a schematic illustration of a delivery system as in FIG. 1 wherein the direction of pulling the clamp supports is shown.
Figure 3:
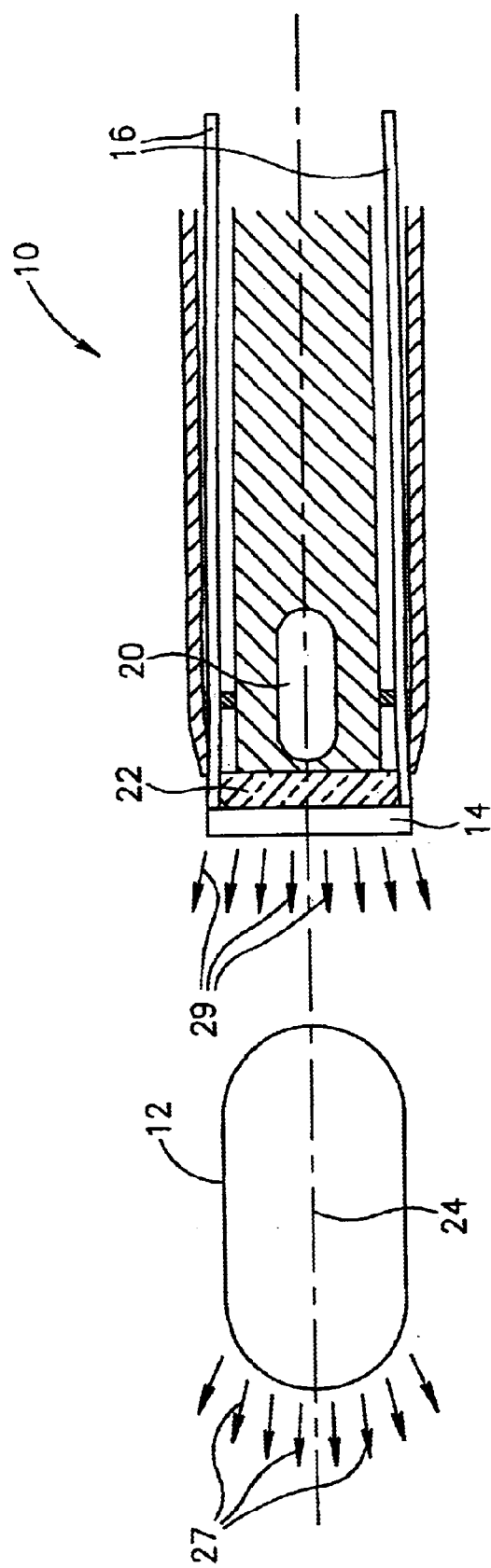
FIG. 3 is a schematic illustration of a detached capsule with fully retracted supports, and the fields of view of both imaging systems is marked in arrows.

FIG. 2 shows the device of FIG. 1 with the ends of the clamp supports 16 shown protruding outside of the patient's body. The arrows 26 indicate the direction of pull needed to bring about the retraction for disengaging the capsule 12. The capsule, being substantially cylindrical, is held snugly by the ring clamp 14. When the clamp's supports 16 are retracted within bore 18, the clamp 14 slides along the smooth surface of the capsule, and eventually loosens its grip on the capsule 12. Thus, the capsule 12 is deposited in position as soon as full retraction of the clamp 14 has taken place. FIG. 2 illustrates the capsule 12 retracted to a stage in which the capsule 12 abuts against the window 22 of the endoscope 10. The window 22 therefore blocks the capsule's further retraction movement, thereby facilitating the sliding of the ring 14 on the capsule's surface. Disengagement of the capsule takes place only as the clamp 14 has slipped by the back end (referenced 32) of the capsule 12, due to the pulling of the supports 16 manually in the direction indicated by arrows 26 away from the capsule 12. This particular situation is shown in FIG. 3, which also shows the capsule 12 detached from the endoscope 10.

An autonomous capsule of an imaging type, such as described in U.S. Pat. No. 5,604,531, can be used to verify its own place of insertion in the G.I. tract as it is pushed along. Once it is deposited, it can continue to acquire images autonomously. FIG. 3, shows the viewing range (arrows 27) of the detached capsule 12, as well as the viewing range (arrows 29) of the imager 20 in the endoscope. The endoscope becomes operative as a camera once the capsule 12 has detached.

In another embodiment of the invention, a tissue sampler, known for its function as an aid in obtaining pieces of tissue out of the G.I, tract, can be used for holding and delivering an autonomous capsule.

Figure 4:
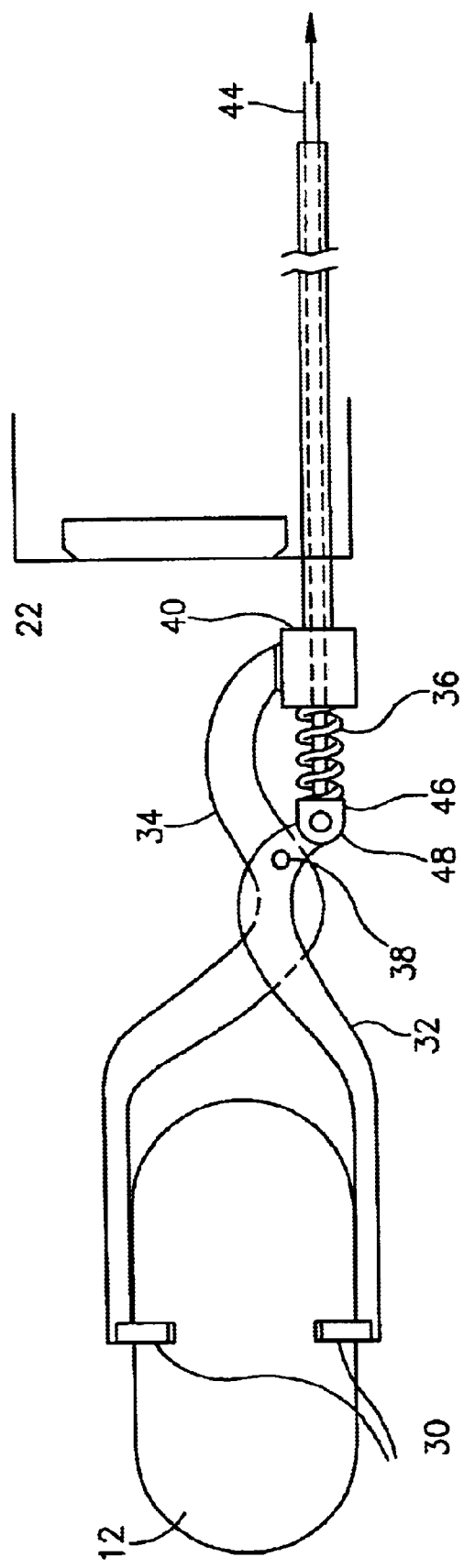
FIG. 4 is a schematic illustration of a delivery system for a capsule, wherein the delivery system has a single cable control mechanism.

In another embodiment of the invention, a single bore endoscope is shown in FIG. 4 to which reference is now made, the release of the capsule clamp is implemented by a single, loosely sheathed cable. In this embodiment, the clamp 30 comprises upper and a lower segments, joined together by a pin 38, which are held by supports 34 and 32, respectively. The upper support 34 is soldered to a sheath 40 of a cable 44, and the lower support 32 is connected via a flexibly pivot 48 to one end 46 of cable 44. A helical spring 36, inserted between cable sheath 40 and cable end 46, to keep them apart.

In operation, the capsule 12 is held by the effect of the support 32 pushing the lower clamp segment upwards. Spring 36 produces a torque through pin 38, such that force is applied inwards by the segments of clamp 30 holding the capsule 12 tightly.

Release of capsule 12 is brought about by pulling cable 44 which, in turn, causes contraction of spring 36 and the torque applied through pin 38 in the direction that causes the clamp segments 30 to loosen their grip around capsule 12.

It will be appreciated that the present invention is not limited by what has been described hereinabove and that numerous modifications, all of which fall within the scope of the present invention, exist. For example, the number of supports of the clamp can be other than described.

It will be appreciated by persons skilled in the art that the present invention is not limited by what has been particularly shown and described herein above.

Rather the scope of the invention is defined by the claims which follow:

1. A method for inserting an autonomous capsule into the G.I. tract by an endoscope, said endoscope having a clamp and at least one retractable support for retaining said clamp, the method comprising the steps of:

engaging said capsule with said clamp;

pushing said capsule to its desired position within the G.I. tract; and disengaging said capsule by loosening the hold of said clamp on said capsule.

2. The method according to claim 1 and further comprising the step of:

verifying the efficacy of said inserting by observing the capsule through an imaging unit placed within said endoscope.

* * * * *